US008425418B2

(12) United States Patent
Suri et al.

(10) Patent No.: US 8,425,418 B2
(45) Date of Patent: Apr. 23, 2013

(54) METHOD OF ULTRASONIC IMAGING AND BIOPSY OF THE PROSTATE

(75) Inventors: Jasjit S. Suri, Roseville, CA (US); Ramkrishnan Narayanan, Nevada City, CA (US)

(73) Assignee: Eigen, LLC, Grass Valley, CA (US)

( * ) Notice: Subject to any disclaimer, the term of this patent is extended or adjusted under 35 U.S.C. 154(b) by 908 days.

(21) Appl. No.: 11/740,807

(22) Filed: Apr. 26, 2007

(65) Prior Publication Data

US 2008/0039723 A1 Feb. 14, 2008

Related U.S. Application Data

(60) Provisional application No. 60/747,565, filed on May 18, 2006, provisional application No. 60/913,178, filed on Apr. 20, 2007.

(51) Int. Cl.
*A61B 8/08* (2006.01)

(52) U.S. Cl.
USPC ............. 600/437; 382/128; 345/634; 706/15; 703/11

(58) Field of Classification Search .......... 345/418–429, 345/619, 629, 630, 634; 382/128, 173, 181, 382/190, 209; 600/437, 439, 407, 443; 706/15, 706/21; 703/11
See application file for complete search history.

(56) References Cited

U.S. PATENT DOCUMENTS

| | | |
|---|---|---|
| 5,282,472 A | 2/1994 | Companion et al. |
| 5,320,101 A | 6/1994 | Faupel et al. |
| 5,383,454 A | 1/1995 | Bucholz |
| 5,398,690 A | 3/1995 | Batten et al. |
| 5,454,371 A | 10/1995 | Fenster et al. |
| 5,531,520 A | 7/1996 | Grimson et al. |
| 5,562,095 A | 10/1996 | Downey et al. |

(Continued)

FOREIGN PATENT DOCUMENTS

| | | |
|---|---|---|
| WO | 0014668 | 3/2000 |
| WO | 2006089426 A1 | 8/2006 |
| WO | 2008062346 A1 | 5/2008 |
| WO | 2008124138 A1 | 10/2008 |

OTHER PUBLICATIONS

Shen et al. Segmentation of Prostate Boundaries from Ultrasound Images Using Statistical Shape Model. IEEE Transactions on Medical Imaging. 22(4):539-551. Apr. 2003.*

(Continued)

*Primary Examiner* — Parikha Mehta
(74) *Attorney, Agent, or Firm* — Marsh Fischmann & Breyfogle LLP; Russell T. Manning (57) ABSTRACT

A system and method (i.e, utility) are disclosed for positioning a needle in three-dimensions based on patient related statistics for extracting tissue during biopsy procedures. Aspects of the utility can be applied independently or serve as an aid to the urologist when regions of interest are hard to discern in an ultrasound image. Regions of interest that correspond to high cancer risk regions (e.g., statistically) are automatically superimposed on an ultrasound image of a patient in real time. Additionally a statistical map based on one or more demographic parameters of a patient and containing cancer probability locations are also automatically mapped on the ultrasound image in real time displaying potential cancer locations. Aspects of the system are also capable of displaying optimal needle placement positions based on statistical priors and will be able to accurately navigate the needle to that position for biopsy extraction and/or treatment.

14 Claims, 10 Drawing Sheets

U.S. PATENT DOCUMENTS

| | | | |
|---|---|---|---|
| 5,611,000 A | 3/1997 | Szeliski et al. |
| 5,810,007 A | 9/1998 | Holupka et al. |
| 5,842,473 A | 12/1998 | Finster et al. |
| 6,092,059 A | 7/2000 | Straforini et al. |
| 6,171,249 B1 | 1/2001 | Chin et al. |
| 6,238,342 B1 | 5/2001 | Feleppa et al. |
| 6,251,072 B1 | 6/2001 | Ladak et al. |
| 6,261,234 B1 | 7/2001 | Lin |
| 6,298,148 B1 | 10/2001 | Cline et al. |
| 6,334,847 B1 | 1/2002 | Fenster et al. |
| 6,342,891 B1 | 1/2002 | Fenster et al. |
| 6,351,660 B1 | 2/2002 | Burke et al. |
| 6,360,027 B1 | 3/2002 | Hossack et al. |
| 6,385,332 B1 | 5/2002 | Zahalka et al. |
| 6,423,009 B1 | 7/2002 | Downey et al. |
| 6,447,477 B2 | 9/2002 | Burney et al. |
| 6,500,123 B1 | 12/2002 | Holloway et al. |
| 6,561,980 B1 | 5/2003 | Gheng et al. |
| 6,567,687 B2 | 5/2003 | Front et al. |
| 6,610,013 B1 | 8/2003 | Fenster et al. |
| 6,611,615 B1 | 8/2003 | Christensen |
| 6,674,916 B1 | 1/2004 | Deman et al. |
| 6,675,032 B2 | 1/2004 | Chen et al. |
| 6,675,211 B1 | 1/2004 | Mamaghani et al. |
| 6,689,065 B2 | 2/2004 | Aksnes et al. |
| 6,778,690 B1 | 8/2004 | Ladak et al. |
| 6,824,516 B2 | 11/2004 | Batten et al. |
| 6,842,638 B1 | 1/2005 | Suri et al. |
| 6,852,081 B2 | 2/2005 | Sumanaweera et al. |
| 6,909,792 B1 | 6/2005 | Carrott et al. |
| 6,952,211 B1 | 10/2005 | Cote et al. |
| 6,985,612 B2 | 1/2006 | Hahn |
| 7,004,904 B2 | 2/2006 | Chalana et al. |
| 7,008,373 B2 | 3/2006 | Stoianovici et al. |
| 7,039,216 B2 | 5/2006 | Shum et al. |
| 7,039,239 B2 | 5/2006 | Loui et al. |
| 7,043,063 B1 | 5/2006 | Noble et al. |
| 7,095,890 B2 | 8/2006 | Paragios et al. |
| 7,119,810 B2 | 10/2006 | Sumanaweera et al. |
| 7,139,601 B2 | 11/2006 | Bucholz et al. |
| 7,148,895 B2 | 12/2006 | Konishi et al. |
| 7,155,316 B2 | 12/2006 | Sutherland et al. |
| 7,162,065 B2 | 1/2007 | Ladak et al. |
| 7,167,760 B2 | 1/2007 | Dawant et al. |
| 7,225,012 B1 | 5/2007 | Susil et al. |
| 7,274,811 B2 | 9/2007 | Sirohey et al. |
| 7,302,092 B1 | 11/2007 | Fenster et al. |
| 7,403,646 B2 | 7/2008 | Sato |
| 2003/0000535 A1 | 1/2003 | Galloway, Jr. et al. |
| 2003/0013951 A1* | 1/2003 | Stefanescu et al. ........... 600/407 |
| 2003/0135115 A1 | 7/2003 | Burdette et al. |
| 2004/0210133 A1 | 10/2004 | Nir |
| 2005/0159676 A1 | 7/2005 | Taylor et al. |
| 2005/0190189 A1 | 9/2005 | Chefd'hotel et al. |
| 2005/0197977 A1 | 9/2005 | Buck et al. |
| 2005/0243087 A1 | 11/2005 | Aharon |
| 2005/0249398 A1 | 11/2005 | Khamene et al. |
| 2006/0002601 A1 | 1/2006 | Fu et al. |
| 2006/0002630 A1 | 1/2006 | Fu et al. |
| 2006/0013482 A1 | 1/2006 | Dawant et al. |
| 2006/0036162 A1 | 2/2006 | Shahidi et al. |
| 2006/0079771 A1 | 4/2006 | Nir |
| 2006/0197837 A1 | 9/2006 | Flath et al. |
| 2006/0227131 A1 | 10/2006 | Schiwietz et al. |
| 2006/0258933 A1 | 11/2006 | Ellis et al. |
| 2007/0014446 A1 | 1/2007 | Sumanaweera et al. |
| 2007/0040830 A1 | 2/2007 | Papageorgiou |
| 2007/0116339 A1 | 5/2007 | Shen |
| 2007/0116381 A1 | 5/2007 | Khamene |
| 2007/0189603 A1 | 8/2007 | Kasperkiewicz et al. |
| 2007/0201611 A1 | 8/2007 | Pratx et al. |
| 2007/0270687 A1 | 11/2007 | Gardi et al. |
| 2008/0002870 A1 | 1/2008 | Farag et al. |
| 2008/0123910 A1 | 5/2008 | Zhu |
| 2008/0123927 A1 | 5/2008 | Miga et al. |
| 2008/0170770 A1 | 7/2008 | Suri et al. |
| 2008/0247616 A1 | 10/2008 | Pescatore et al. |
| 2009/0093715 A1 | 4/2009 | Downey et al. |

OTHER PUBLICATIONS

Shen et al. Optimized prostate biopsy via a statistical atlas of cancer spatial distribution. Medical Image Analysis. 8:139-150. 2004.*

* cited by examiner

2D Image Storage

FIG. 3A

3D Volume Image

METHOD OF ULTRASONIC IMAGING AND BIOPSY OF THE PROSTATE

CROSS REFERENCE TO RELATED APPLICATIONS

This application claims priority under 35 U.S.C. §119 to U.S. Provisional Application No. 60/747,565 entitled "Prostate Target Identification System" having a filing date of May 18, 2006 and U.S. Provisional Application No. 60/913,178 entitled "An Improved Method for 3-D Biopsy" having a filing date of Apr. 20, 2007; the entire contents of both of these applications are incorporated by reference herein.

FIELD

The present invention relates to medical imaging. One aspect is directed to image guided surgery using 3D patient related statistics. One application is in aiding a urologist during prostate biopsy to find potential cancerous tissue sites for extraction often in the absence of any significant features or distinguishing characteristics of cancers in 3D ultrasound images.

BACKGROUND

The Center for Prostate Disease Research (CPDR) has projected that there will be over 200,000 new cancer cases and 27,000 deaths from prostate cancer in the year 2007. Prostate cancer alone accounts for roughly 29% of cancer incidences in men. According to the National Cancer Institute (NCI), a man's chance of developing prostate cancer increases drastically from 1 in 10,000 before age 39 to 1 in 45 between 40-59 and 1 in 7 after age 60. The overall probability of developing prostate cancer from birth to death being close to 1 in 6.

Traditionally either elevated Prostate Specific Antigen (PSA) level or Digital Rectal Examination (DRE) has been widely used as a standard for prostate cancer detection. For a physician to diagnose prostate cancer, a biopsy of the prostate must be performed. This is done on patients that have either abnormal PSA levels or an irregular digital rectal exam (DRE), or on patients that have had previous negative biopsies but continue to have elevated PSA. Biopsy of the prostate requires that a number of tissue samples (i.e, cores) be obtained from various regions of the prostate. For instance, the prostate may be divided into six regions (i.e., sextant biopsy), apex, mid and base bilaterally, and one representative sample is randomly obtained from each sextant. Such random sampling continues to be the most commonly practiced method although it has received criticism in recent years on its inability to sample regions where there might be significant volumes of malignant tissues resulting in high false negative detection rates. Further using such random sampling it is estimated that the false negative rate is about 30% on the first biopsy. That is, 30% of the men had cancer, but the biopsy procedure missed finding it. Thus, many men will require a second and sometimes a third prostate biopsy, at the discretion of their physician. This can result in increased patient anxiety, health care costs, and/or delayed cancer diagnosis.

Accordingly, to improve the detection of cancer during biopsy, researchers have discussed different sampling schemes as well as using more cores or sampling different regions for improving detection rates. In the latter regard, it has been proposed to obtain samples from additional regions (e.g., 10 core biopsy) not sampled by standard sextant biopsy. Others have noted the difference in cancer likelihood in the different zones of the prostate (e.g. inhomogeneous distribution) and proposed more complete sampling of regions that have a higher likelihood of being cancerous. In addition to studies verifying inhomogeneous spatial distribution of cancers there is also the possibility of cancers occurring in specific regions based on age, PSA level and ethnicity.

SUMMARY OF THE INVENTION

To perform a biopsy of a prostate, an image (e.g., 3-D ultrasound image) may be acquired and utilized to guide a biopsy needle to locations on or within the prostate. The present inventors have recognized that the ability to combine statistical data (e.g., cancer data by prostate region) with the image may allow medical personnel to obtain biopsy cores from (or perform procedures on) regions of the prostate having a greater probability of containing cancerous cells if cancer is indeed present. More specifically, it has been determined that the occurrence and location of a number of prostate cancers may be based on one or more demographic characteristics (e.g., age, ethnicity, etc.) and that by utilizing such information, the effectiveness of a biopsy procedure may be improved.

That is, the systems and method (i.e, utilities) discussed herein use previously gathered statistical information regarding various zones within the prostate where cancer resides and a probability map of cancer locations from expert (histologist) based ground truth selection. There are several utilities that may work together to arrive at a 3D target site for biopsy sampling. Initially, a prostate is identified within an ultrasound volume. The identified prostate is mapped, in real time, to a shape model whose contents include statistical information and/or zone related information that is previously determined and stored. Accordingly, one utility involves the training of a prostate shape model and the corresponding association of statistical information with the shape model and another utility involves fitting the shape model to fit patient image/data and the transfer of statistical information from the shape model to the patient image. Such a shape model may be a 3D model such that it can be fit to a 3D ultrasound image. Accordingly, such statistical data may be transferred to locations within the 3D ultrasound image as well as onto the surface of the image.

The statistical information transferred to the patient image/data may contain information regarding the various zones of the prostate and also cancer probability maps specific to patient related data (age, PSA level and ethnicity). Such data (e.g., cancer probability maps) may allow targeting or treating areas/regions to specific to each patient while still focusing on zones where cancers are most prevalent. For instance, such statistical data may be overlaid onto the patient image to allow guiding a biopsy device to a region that is statistically at risk for cancer based on one or more patient specific parameters including, without limitation, demographic parameters (age, ethnicity, etc.), PSA levels etc. As utilized herein, overlaid includes the incorporation of statistical data onto and/or into a 3D patient image as well as onto 2D patient images.

Statistics are generated from a large database of ground truth images. The procedure begins with the collection of data from histology specimens that are outlined and labeled. These labels correspond to whether cancer is present or not at a 3-D location. Several such samples are collected are used to compile statistics on the presence of cancer locations. The database of such images whose cancer characteristics are known is referred to as ground truth data. These ground truth images are all fitted to a common anatomical frame that contains labels that mark landmark locations of the prostate, whether cancer is present or not. Cancer probability maps are then computed from this data and a cancer probability map/atlas or more generally look-up-table (i.e., LUT) is created. This LUT can be used for biopsy guidance.

When a new patient comes in for biopsy, the acquired 3-D ultrasound image is fit to the LUT (which could be an image in which the LUT resides) or vice versa. For instance, the image including the LUT may be a shape model that is fit to an acquired ultrasound image. Once the patient image is fit to this model, 3-D statistical data associated with the LUT, including statistical locations of interest, is available (e.g., displayed on and/or within) with the acquired 3-D ultrasound image and can be used to perform biopsy procedures.

A shape model may be generated from a database of ultrasound volumes. Such ultrasound volumes may be compiled and segmented either manually or using a segmentation program to obtain several prostate ultrasound surfaces. These surfaces can be used to train a shape model. A shape model may include a mean shape and one or more vectors (e.g., Eigen vectors) that correspond to the principal modes of variation. The projections on these vectors can then be used to describe any shape resembling the training data accurately. The advantage of using shape models is that these projections may represent the direction of largest variance of the data. For instance, 10-15 such projections may adequately represent a large range of shapes accounting for more than 95% of the variance in the data. The projections can be either directly optimized to maximize the similarity between the given shape and the model or the model can be allowed to warp freely and can then be constrained by the requirements of the model that prevent the model from fitting (e.g., warping) into shapes that do not resemble a prostate.

Accordingly, one aspect includes obtaining an ultrasound image of a prostate of a patient and fitting a predetermined prostate shape model to that image. Statistical data is then transferred from the prostate shape model to the ultrasound image such that one or more procedures may be performed on the prostate based on the statistical data. For instance, such a procedure may include obtaining at least one biopsy sample from a location of interest within the prostate and/or placing objects within the prostate.

Transferring data may include any method of overlaying statistical data onto the ultrasound image of the prostate. When three-dimensional shape models and prostate images are utilized, such overlaying of statistical data may include orienting regions and/or markers associated with statistical data within the three-dimensional ultrasound image. Likewise, information may be overlaid onto the surface of the three-dimensional image. It will be further recognized that such three-dimensional images may be sliced to provide two-dimensional images on which statistical information is present.

In one arrangement, performing the procedure includes selecting one or more potentially cancerous regions for biopsy and obtaining a biopsy sample from the selected regions. In conjunction with such performance, the method may include establishing one or more biomarkers on the prostate. Such biomarkers may represent biopsy locations statistically associated with cancer. For instance, the statistical data may include one or more regions that are associated with cancer. A centroid of such regions may be associated with an optimal target location (e.g., biomarker) for obtaining a biopsy sample Accordingly, information from the ultrasound image (e.g., biomarker) may be provided to a guidance instrument for use in guiding a biopsy needle to a location on and/or within the prostate.

In a further arrangement, transferring statistical data includes transferring prostate zone information to the ultrasound image. In this regard, the prostate may include various different zones, and statistical size averages associated with such zones may be overlaid onto an ultrasound image. Further statistical histological data associated with each zone may be provided. Accordingly, procedures, such as biopsy, may be performed zone by zone, for example, sequentially.

In a further arrangement, statistical data may be associated with specific patient data. In this regard, statistical data based on one or more demographic factors and/or PSA levels may be utilized to select statistical data that is more relevant to a particular patient. In this regard, it is noted that various forms of cancers originate in different locations based on ethnicity and/or other factors. In this regard, by selecting more relevant statistical data and/or associating that data with the shape model, or, providing multiple shape models with different statistical data, improved biopsy may be provided.

DETAILED DESCRIPTION

Reference will now be made to the accompanying drawings, which assist in illustrating the various pertinent features of the present disclosure. Although the present disclosure is described primarily in conjunction with transrectal ultrasound imaging for prostate imaging, it should be expressly understood that aspects of the present invention may be applicable to other medical imaging applications. In this regard, the following description is presented for purposes of illustration and description.

Presented herein are systems and processes (utilities) to aid urologists (or other medical personnel) in finding optimal target sites for biopsy. Generally, the utilities use statistical information regarding various zones within a prostate where the cancer resides and/or probability maps of cancer locations obtained from an expert (histologist) based ground truth selection. There are several procedures, each of which may include separately novel features, within the utilities that may work together to arrive at the identification of statistically important 3-D target sites. The utilities begin with identifying the prostate first within an ultrasound volume. The identified prostate image (e.g., segmented prostate) is mapped to a previously generated model that includes statistical information in the form of ground truth locations and/or zone related information. The mapping/fitting of the prostate image to the model is achieved in real time and statistical information may be applied to the prostate image such that the statistical information may be utilized for performing one or more procedures (e.g., biopsy, brachytherapy, etc.).

Figure 1:
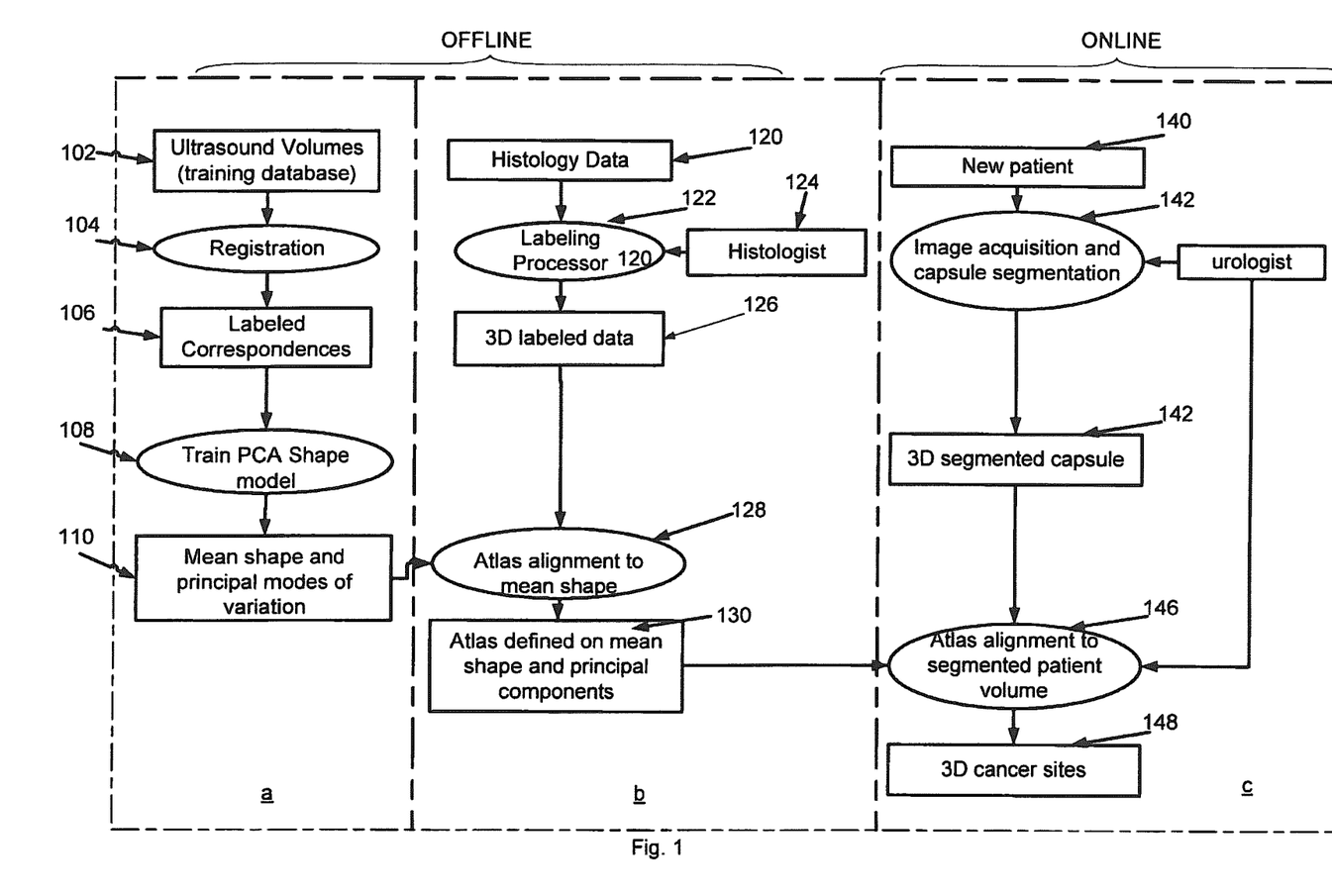
FIG. 1 illustrates processes for generating a shape model, incorporating statistical information into the shape model and applying the shape model to a prostate image.

As illustrated in FIG. 1, there are three main processes in implementing the utility for identifying biopsy locations: a) generation and training of a shape model; b) statistical information collection and combination with the shape model and c) fitting the shape model to patient data and transferring statistical information. However, it will be appreciated that implementing the system may include various sub-processes. For purposes of the discussion herein, the term 'offline' is meant to refer to procedures performed prior to a patient visit and the term 'online' is meant to refer to procedures performed during a patient visit. Each of these processes and/or sub-processes contains one or more novel aspects alone as well as in combination with the other processes/sub-processes. Accordingly, each process is discussed herein.

Shape Model

Figure 2:
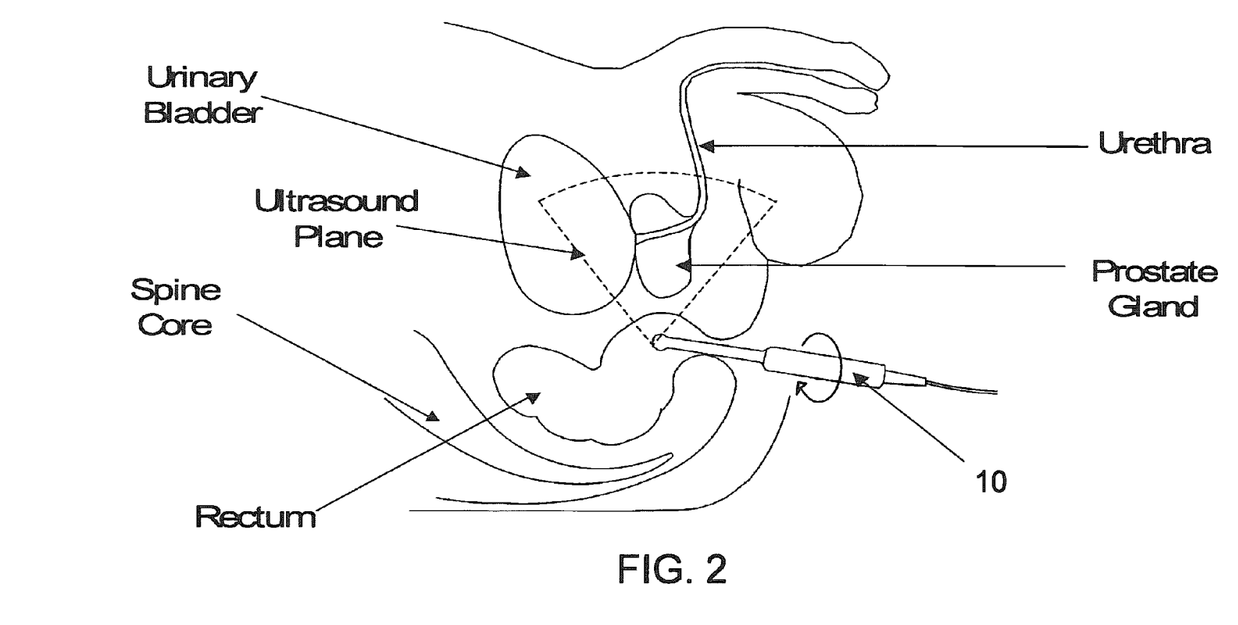
FIG. 2 illustrates obtaining a prostate image.
Figure 3A:
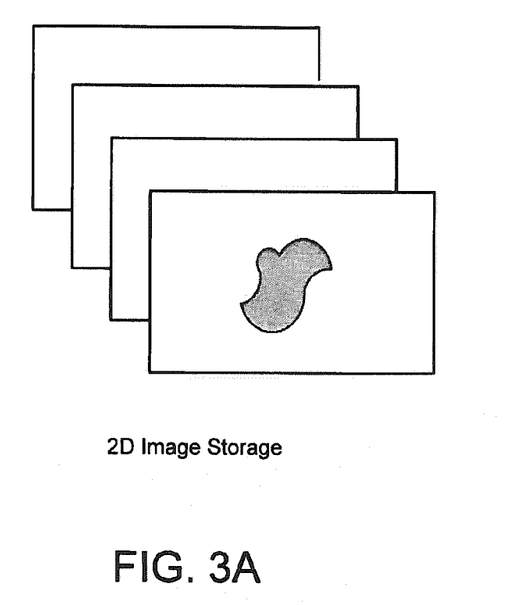
FIGS. 3A and 3B illustrate 2D and 3D prostate images.
Figure 3B:
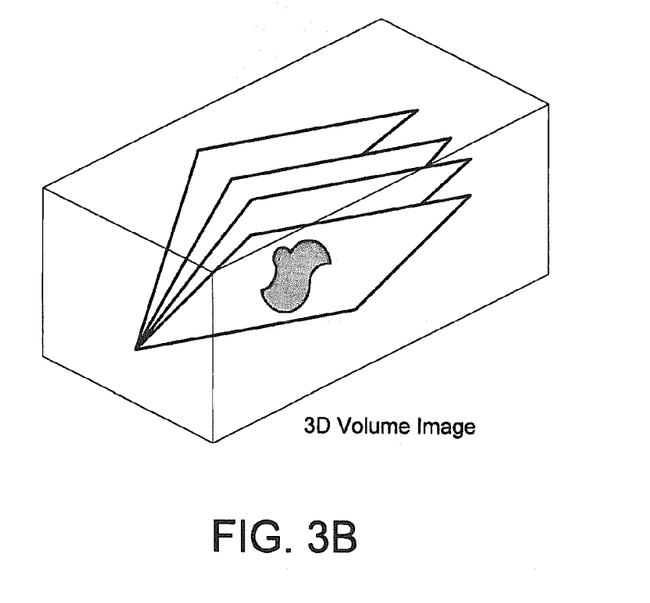

Initially, 3-D ultrasound images of multiple prostates are acquired 102 using, for example a TransRectal UltraSound (TRUS) system. The acquired images may then be converted to 3-D orthogonal voxel data (e.g., ultrasound volumes) having equal resolution in all three dimensions. The images may be acquired in an appropriate manner. FIG. 2 illustrates a transrectal ultrasound probe being utilized to obtain a plurality of two-dimensional ultrasound images of a prostate 12. As shown, the probe 10 may be operative to automatically scan an area of interest. In such an arrangement, a user may rotate the acquisition end 14 of the ultrasound probe 10 over an area of interest. Accordingly, the probe 10 may acquire plurality of individual images while being rotated over the area of interest. See FIGS. 3A-B. Each of these individual images may be represented as a two-dimensional image. See FIG. 3A. Initially, such images may be in a polar coordinate system. In such an instance, it may be beneficial for processing to translate these images into a rectangular coordinate system. In any case, the two-dimensional images may be combined to generate a 3-D image. See FIG. 3B. As will be appreciated, such a procedure may be performed on a plurality of patients to obtain a database of ultrasound volumes, which may be utilized to generate a shape model.

Referring again to FIG. 1, once the ultrasound volumes are obtained 102, compiled and segmented, either manually or using a segmentation program, the ultrasound volumes may be utilized to train a shape model. However, prior to training the shape model, the segmented surfaces must be labeled. That is, corresponding structures within each segmented surface must be labeled to a common reference frame. This is referred to as a registration process 104. See FIG. 1. In this regard, each of the ultrasound volumes are marked by an expert (e.g., histologist) in feature rich regions or regions that distinguish the shape of the surface. The marked points are called landmarks, and they are correspondingly marked in all of the images of the training data/ultrasound volume database.

Figure 4:
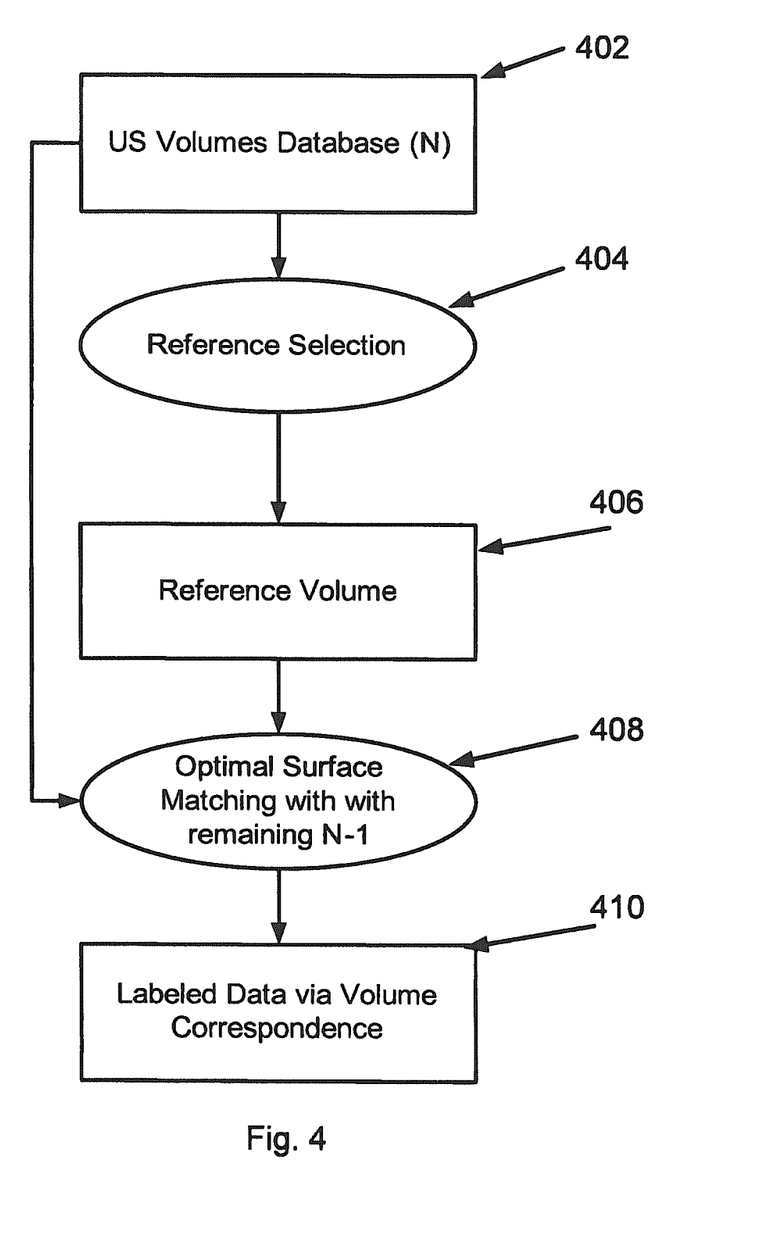
FIG. 4 illustrates a process for labeling ultrasound volumes.

FIG. 4 illustrates a process utilized in the current embodiment where a non-linear registration method is utilized to align all the images to a common reference. In this regard, the ultrasound volume database is provided 402. A reference image is selected 404 from the ultrasound database 402. This image may be randomly picked from the ultrasound volume database 402. The remaining volumes (n−1) are all aligned 408 with the reference volume 406 associated with the selected image. This alignment is non-linear and may result in a point wise correspondence from one surface to the other, resulting in labeled data 410. That is, all of the common landmarks of the ultrasound volumes are aligned with a chosen reference surface from the database. The resulting aligned images or 'labeled correspondences' 106 (See FIG. 1) may then be utilized to train the shape model 108.

Figure 5:
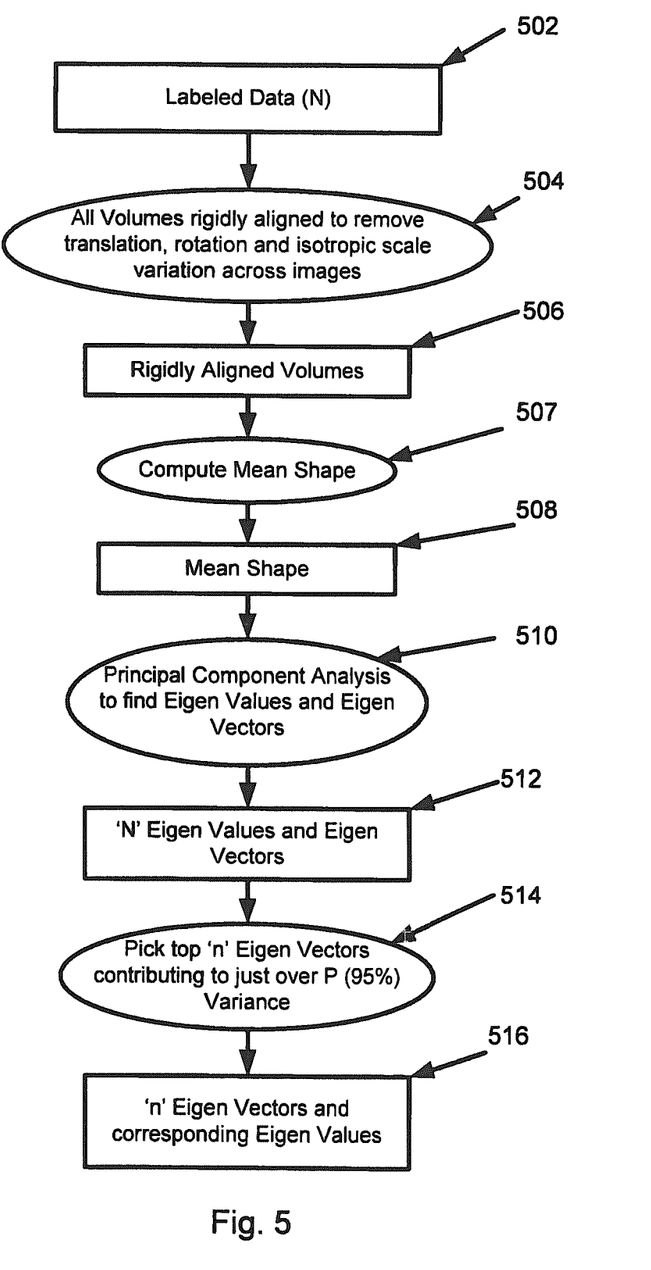
FIG. 5 illustrates a process for generating a shape model.

A process for training the shape model is provided in FIG. 5. As will be appreciated, the training images (i.e., labeled data 502) reflect a variety of different geometrical prostate shapes. These different shapes must be taken into account in training the system. To this end, an average shape is created from the training images in the form of a mean shape vector. Generally, creating the average prostate shape involves labeling a set of feature points corresponding to prostate features/landmarks depicted in each training image in the training set of ultrasound volumes. The locations of the labeled feature points from a training images are used to form vector shapes. The average of all the vectors is then computed to produce a mean vector shape that represents the average prostate shape.

The ultrasound volumes associated with the labeled data 502 are then Procrustes aligned so as to remove variations in translation, rotation and scaling across the dataset in order to move them into a common frame of reference. Such alignment 504 results in rigidly aligned training volumes 506. Once the volumes are aligned, a mean shape may be computed 507 to generate a mean shape 508. In the present arrangement, a principle component analysis (PCA) is performed 510 to identify Eigen values and Eigen vectors 512 that account for the variance in the set of images. A top percentage of the Eigen Vectors are selected 514 that account for more than 95% variance of the entire set of images. Accordingly, the projections on the selected Eigen Vectors 516 can then be utilized to align the shape model (i.e., mean shape) to any other shape.

That is, a mean shape and its principal mode of variation are defined 110 (See FIG. 1). These modes of variation can be utilized to fit the mean prostate shape to a prostate image acquired from a patient. Registration of the model to any shape resembling the training shape now becomes a straightforward mathematical process. The projection can be either directly optimized to maximize the similarity between the given shape and the model or the model can be allowed to "warp" freely and may be constrained by requirements of the model that would prevent the model from warping into shapes that do not resemble a prostate. This can in fact be construed as a segmentation problem where a model can be used to warp so as to minimize energy based on the constraints of the shape model or as a registration problem, which is the case where the model is warped so as to best match a segmented prostate surface.

Statistical Information Collection.

Statistical information collection entails the collection of histology data 120, which are outlined and labeled 122. See FIG. 1. In this regard, prostate cancer locations are identified and mapped for a large group of patient data. These samples are collected and used to compile statistics on the presence of cancer locations. Reference to the database of images whose cancer characteristics are fully known is referred to as ground truth data. This ground truth data may be utilized to generate a look-up-table or LUT/map/atlas that indicates the probability of various regions of developing cancer. These ground truth images may be generated from histological data including histological slices from actual prostates and/or histological data identified from individual (e.g., 2-D) prostate images. The ground truth images are all mapped to a common anatomical frame and contain labels that mark every location of the prostate, i.e. whether cancer is present or not. Such labels may be selected by a histologist 124. Cancer probability maps/atlases are then computed from this data. These maps/atlases can be used for biopsy guidance.

The specificity of the map/atlas may be further improved by normalizing subgroups of the data separately based on age, ethnicity, PSA levels and/or other demographic factors. In this regard, statistical information may be based on one or more demographic parameters. In any case, cancer probability maps/atlases are computed from histological data which may include actual prostates that have been removed from cancer patients as well as from images of cancerous prostates (e.g., samples). The cancer in the samples may be mapped by a histologist who reviews the sample identifies the location of cancer therein. Accordingly, a database may be generated from a plurality of such prostates to identify which regions of the prostates are likely to identify which regions of the prostates are likely to have cancer (e.g., based on one or more demographics), as well as to identify the exact location of such cancer.

Data from separate prostates is labeled to a common reference frame such that the data may be incorporated into a map/atlas that may be utilized to identify areas within a prostate for a given patient. Such labeling may include selecting a volume as a common volume of reference for a set of image volumes. Each of the remaining volumes may be registered to the chosen common volume of reference so as to create an atlas. Then, special coordinates of cancer in each of the remaining image volumes are mapped onto the atlas coordinates in the atlas by transformation that registers the corresponding image volume to the atlas.

In this regard, prostate regions that contain cancer may be identified. For instance, if a plurality of the histological samples of different prostates include cancer in a common region, a centroid of that region may be identified. The centroid may be a common point or biomarker of all the map/atlas coordinates and may represent an optimal target position for biopsy to identify cancer within that region of the prostate. That is, the centroid/biomarker may identify an optimal position for sampling for a patient having demographic information and/or PSA levels that match those of a given map/atlas.

In any case, once the histological data is labeled into a common 3D reference frame 126, a map/atlas may be aligned 128 with the mean shape of the shape model discussed above. That is, statistical information of the map/atlas (e.g., regions of increased probability of cancer) may be incorporated into the shape model. This shape model and corresponding statistical information 130 may then be fit to an image of a prostate of a patient in an online procedure. Accordingly, statistical information associated with the regions having a high incidence of cancer may be overlaid onto the surface of the image of the prostate of the patient. Accordingly, these regions may be targeted for biopsy.

Fitting the Shape Model to Patient Image

As illustrated in FIG. 1, the online portion of the utility involves acquiring an image 140 for a new patient. This may be performed as illustrated in FIG. 2 where a side fire or end fire TRUS probe 10 is utilized to acquire a patient prostate image. However, it will be appreciated that other probes may be may be utilized as well. The probe 10 may also includes a biopsy gun (not shown) that may be attached to the probe. Such a biopsy gun may include a spring driven needle that is operative to obtain a core from desired area within the prostate. In this regard, it may be desirable to generate an image of the prostate 12 while the probe 10 remains positioned relative to the prostate as well as identify target areas for sampling. Further, it may be desirable to register the location of the probe and or needle to the ultrasound images, such that the images may be utilized to direct the needle to an area or/and within the prostate for obtaining a core sample.

In any case, once the ultrasound image is acquired it may be segmented 142 to identify the surface of the 3-D volume/capsule 144 and/or the boundaries of individual 2-D images. Such segmentation may be performed in any known manner.

One such segmentation method is provided in co-pending U.S. patent application Ser. No. 11/615,596, entitled "Object Recognition System for Medical Imaging" filed on Dec. 22, 2006, the contents of which are incorporated by reference herein. The segmented image is then provided for combination with the shape model 146 in order to align the map/atlas information with the acquired image. Biopsy locations may then be identified 148.

Figure 6A:
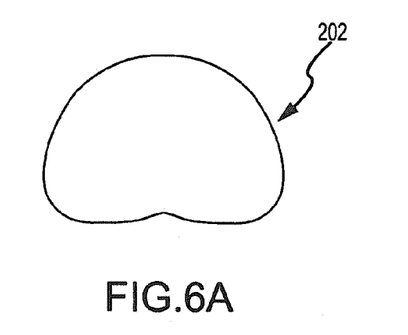
FIGS. 6A-6E illustrate application of a shape model and statistical data to an ultrasound image.
Figure 6B:
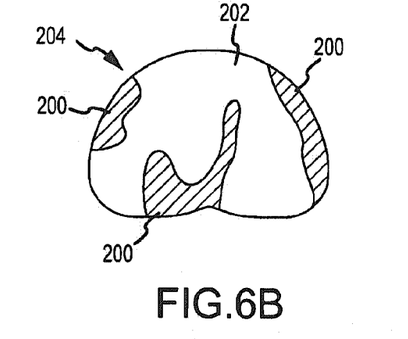
Figure 6C:
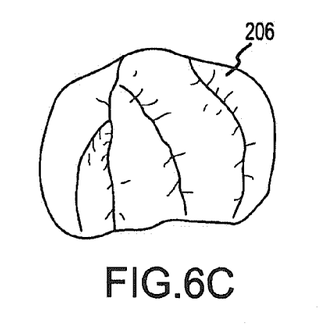
Figure 6D:
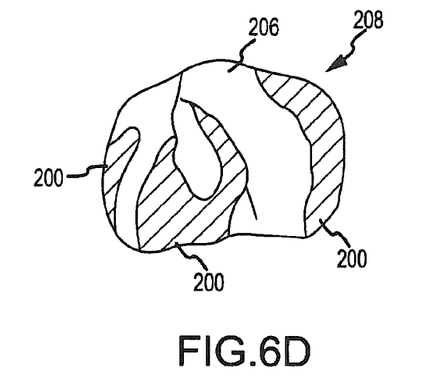

FIGS. 6A-6E graphically illustrate the overall process. Though illustrated as 2D figures, it will be appreciated that the shape model, prostate image, statistical regions and biomarkers discussed herein may be three dimensional. Accordingly, the statistical information and biomarkers may be displayed on and/or within the prostate image. Initially, the shape model 202 is provided 6A. Statistical information 200 (e.g., ground truth data) corresponding to a current patient (e.g., based on demographics, PSA etc) is aligned with the shape model 202 so that a completely defined geometrical deformation shape model 204 including statistical information is provided. FIG. 6B. The deformation shape model 204 may be based on a set of Eigen vectors that allow the model 204 to only be fitted in ways allowed by predetermined limitations of the model. The model may then be applied (e.g., fit) to an acquired ultrasound prostate image 206. FIG. 6C. The result of this fitting procedure is also the transfer of statistical information to the prostate image 206 of the patient. That is, the statistical information may be applied to the prostate image 206 of the patient to provide a combined image with statistical data 208. FIG. 6D. A urologist may utilize the combined image 208 to identify regions on the prostate of the current patient that have, for example, higher likelihood of cancer. Accordingly, the urologist may target such regions for biopsy.

Figure 6E:
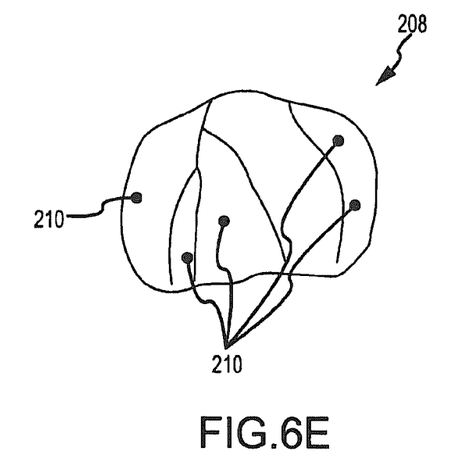

The identification of target locations (e.g., biomarkers) may allow for use of a positioning system to obtain biopsies from those locations. In this regard, a urologist may use 3-D cancer distribution and/or biomarkers for needle positioning during biopsy. That is, the statistical information applied to the prostate may be reduced into a biomarker framework to generate the cancer biopsy spots as surrogate biomarkers for biopsy. See FIG. 6E. The concept comes from knowledge of the centroid/central core of the cancer for a 3D cancer region. Since the 3D model will have different 3D regions, one can reduce the 3D regions into 3D centralized spots as biomarkers for biopsy. The reduction of the 3D cancer regions into biomarkers is illustrated in FIG. 6E. As shown, the biomarkers 210 (e.g., a centroid of potentially cancerous region) are displayed on the on the combined image 208 that provide a target location for biopsy. Further, it will be appreciated that the location of these biomarkers as applied to the prostate image may be output from, for example the imaging device to a positioning device. The positioning device may then guide a biopsy device (e.g., needle) to the biomarker. Such a biopsy device may be incorporated onto, for example, a TRUS ultrasound.

Figure 7:
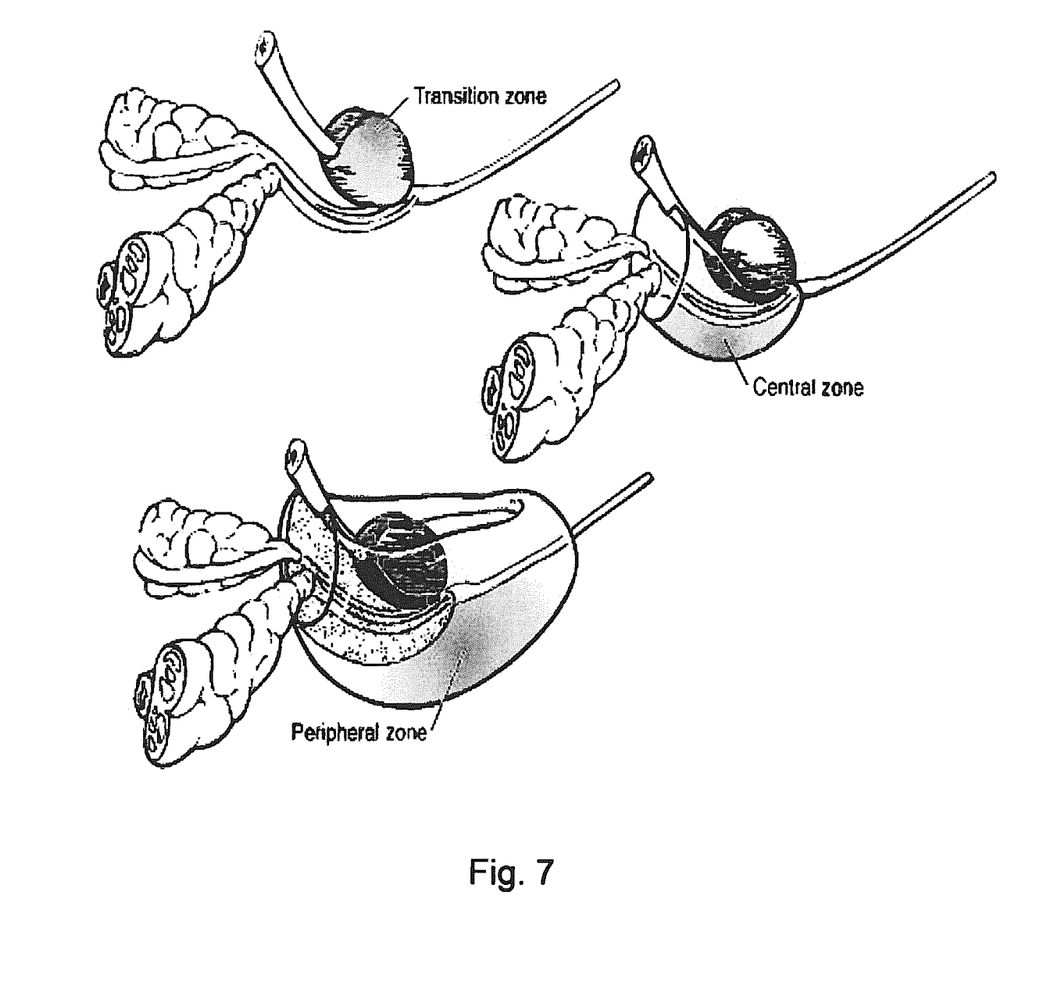
FIG. 7 illustrates various zones of prostate.

The provision of a system that allows for combining statistical information with an image of a patient's prostate may allow for additional enhanced procedures. For instance, the prostate is formed of three zones including a peripheral zone, a central zone and a transition zone. See FIG. 7. Since cancer is most often found in the peripheral zone of the prostate, followed by transition and central zones, biopsy can be performed starting in order of the likelihood of cancer. That is, zonal targeting of biopsy sites can be used to improve the specificity of diagnosis and/or treatment.

Figure 8A:
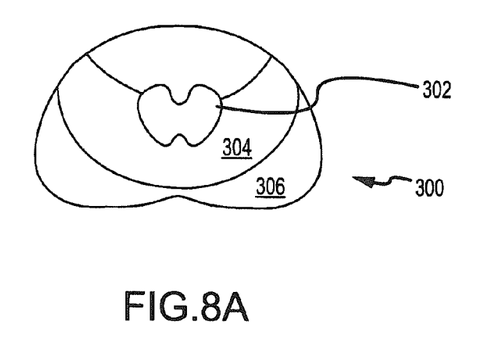
FIGS. 8A-C illustrate application of zone information to a prostate image.
Figure 8B:
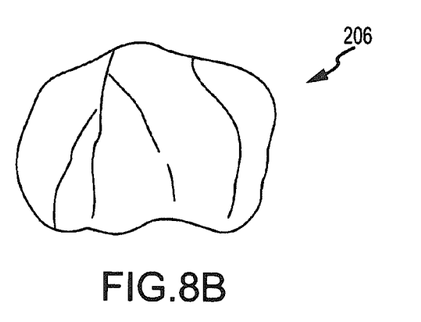
Figure 8C:
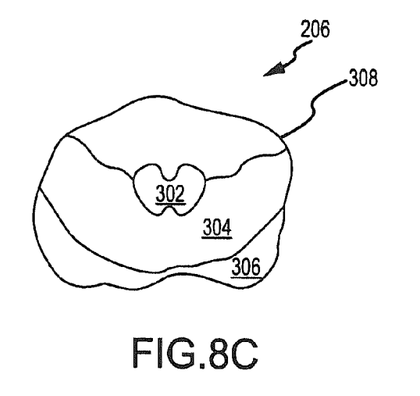

In order to allow targeting individual zones within a patient's prostate, the shape model discussed above may also include zonal information. In this regard, during the generation and training of the shape model, data associated with the transitional zone, central zone and/or peripheral zones of multiple prostates may be incorporated into the shape model such that such information may be applied to the prostate image. For instance, as shown in FIGS. 8A-8C, the transition zone 302, central zone 304 and peripheral zone 306 may be incorporated into a shape model 300. The shape model may also include statistical information as discussed above. Again, an ultrasound image of a prostate 206 of a patient may be acquired. See FIG. 8B. In this arrangement, in addition to applying statistical information regarding cancer locations onto the prostate 206, the shape model 300, including the zone information, may be overlaid onto the prostate 206. In this regard the resulting three-dimensional image may be segmented in order to generate views in which the different zones within the prostate are visible. See FIG. 8C.

Figure 9:
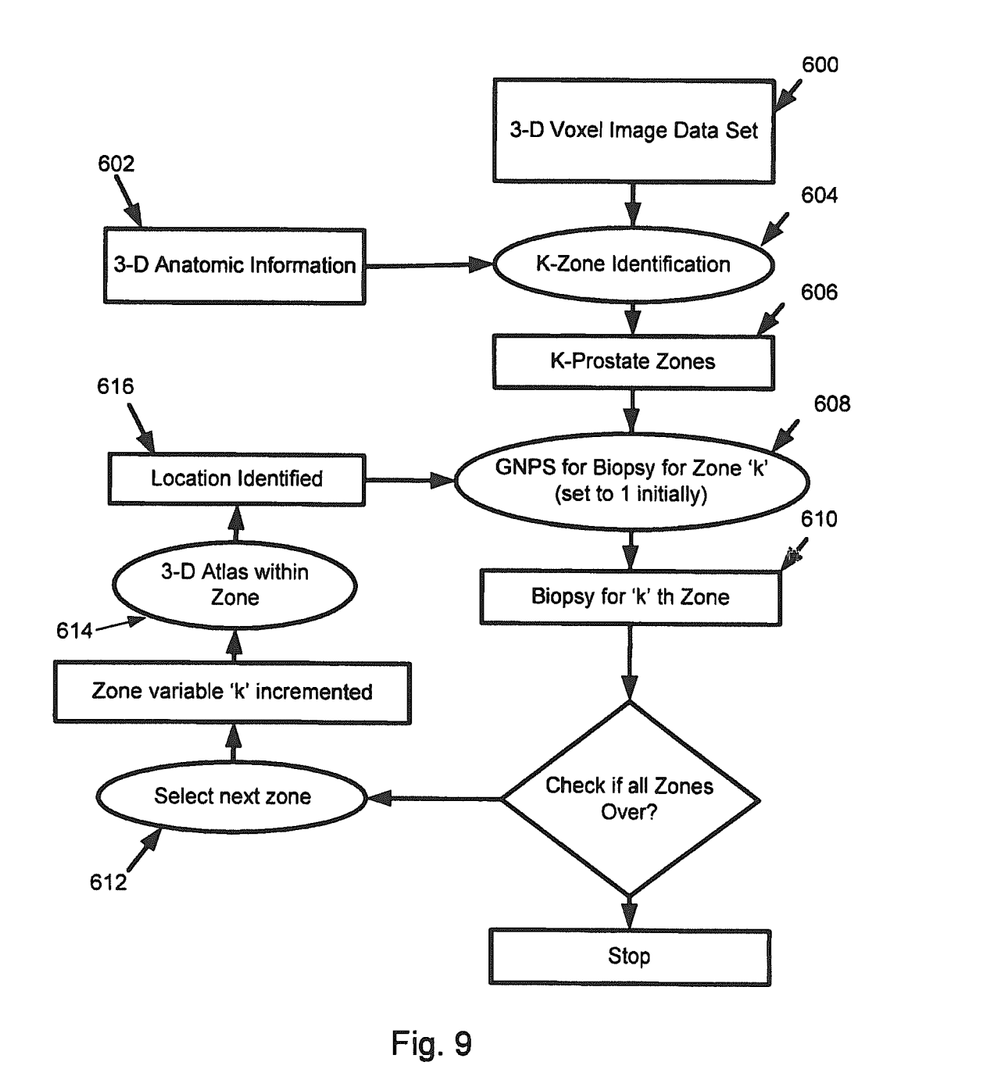
FIG. 9 illustrates a zonal biopsy procedure.

The combined view 308 may then be utilized to identify areas within specific zones for biopsy purposes. In one arrangement, the use of such zones may allow for sequential identification of target locations. In this regard, the zones may be identified sequentially within the patient's prostate. Further, these zones may be selected in the order of importance. In any case, three-dimensional locations within a zone may be ascertained through use of an atlas/map containing statistical information regarding that zonal area. Accordingly, regions of interest within the zone and/or biomarkers may be generated for the zone and may identify one or more points of maximum likelihood for cancer based on the map/atlas. Accordingly, a biopsy of this location may be performed. FIG. 9 illustrates an overall process for performing a zonal biopsy. The method starts with the obtaining 600 an ultrasound image of a prostate of a patient. In addition, the patient's information is entered (PSA, age, ethnicity and/or others) and an atlas or look-up table specific to these statistics is retrieved 602 from a database. In any case, the patient's ultrasound image is acquired, interpolated and reconstructed into 3D. The reconstructed image may then be segmented by any of several segmentation techniques to get a surface outline of the ultrasound prostate. The patient's surface is then aligned with the zones one at a time. In this regard, zones for sampling are selected 604. For each zone selected 606, statistical information from the map/atlas are utilized to identify 608 optimal location for biopsy based on the retrieved statistical data for that zone. A biopsy needle may be guided to the location to obtain a biopsy sample 610. If another zone is selected 612, a 3D atlas for that zone may be obtained 614 and utilized to identify 616 one or more target locations for the current zone. This may be repeated until all selected zones in the prostate are sampled.

In addition to the above noted functions, the disclosed processes, alone or in combination, also provide one or more of the following advantages. As statistical properties of cancerous regions in a prostate are derived in the 3-D regions, the maps/atlases include all information necessary to guide a biopsy planning process. Further, as the maps/atlases are prepared offline prior to patient visits, this allows the statistical data of the maps/atlases to be quickly selected (e.g., based on demographics, etc.) and applied to an acquired image. Further, as a result of matching the map/atlas to a patient based on patient specific information, the probability of identifying cancerous cells in improved. Further, the utility may allow for the comparison of images a prostate of a patient where the images are acquired at separate times. That is, the utility may allow for the registration of temporally distinct images together. This may allow, for example, comparison of the overall size of the prostate to identify changes. Further, this may allow for identifying previous biopsy locations, obtaining biopsies form previous locations and/or utilizing old biopsy locations to permit sampling of previously unsampled regions.

In a system that uses biomarkers as location identifiers, cancerous regions derived from the histology data may be reduced to 3-D target locations by computing the center of the originating cancers. These biomarkers may accurately represent changes during which a cancer has evolved or spread over a 3-D region. Further, the computation of biomarkers is an offline process and it does not affect the workflow of urologists for biopsy. Another advantage of having the biomarker strategy is that it avoids the occlusion of the prostate image during biopsy.

As noted above, sextant biopsy can miss 30% of cancers and other biopsy methods have randomly obtained biopsy samples from all zones of the prostate. Since a majority of cancers are found in the peripheral zone of the prostate, following a zonal concept of biopsy sampling can be very efficient. That is, zones having higher likelihood of cancer may provide a majority or all biopsy samples. Further, combining zonal biopsy with biomarkers provides the added advantage of finding target locations accurately and also improves the efficiency of a biopsy process. That is, the areas (zones) targeted for biopsy sampling may be reduced based on patient specific information and locations within the zones may be limited to those identified as having high probability of cancer. The combined effect of biomarker identifying target locations based on statistical data and obtaining biopsies in a zonal fashion can make the overall biopsy process very efficient while allowing for improved cancer detection.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method for use in medical imaging, comprising:
providing a deformable prostate shape model comprising an average shape of a plurality of prostate images obtained from a plurality of patients;
obtaining a cancer probability map from prostate cancer statistics of a plurality of patients, wherein the cancer probability map identifies at least one region of a prostate having an increased probability of cancer;
aligning said cancer probability map with said deformable prostate shape model to obtain a deformable prostate shape model having cancer probability statistics;
obtaining an ultrasound image of a prostate of a current patient;
segmenting said ultrasound image of said current patient to identify a boundary of said prostate of said current patient;
fitting the deformable prostate shape model having cancer probability statistics to the boundary of the segmented prostate image so that said at least one region having an increased probability of cancer is overlaid onto the ultrasound image of said prostate of said current patient;

establishing at least one biomarker on said at least one region of said shape model, wherein said at least one biomarker represents a biopsy location statistically associated with cancer;

presenting, on a display, the ultrasound image of said current patient with said at least one biomarker; and performing a procedure on the prostate of the current patient based on the at least one biomarker in the presented ultrasound image of the current patient.

2. The method of claim 1, wherein performing a procedure comprises:

using said at least one biomarker as a target location for a biopsy sample of said prostate; and obtaining at least one biopsy sample from the prostate based on said target location.

3. The method of claim 1, wherein performing a procedure comprises selecting one or more of the regions statistically likely to have cancer for biopsy and obtaining a biopsy sample from selected regions.

4. The method of claim 1, wherein the steps of obtaining, fitting, transferring and performing are performed during a single procedure.

5. The method of claim 1, further comprising:

utilizing a plurality of prostate images to generate the shape model and one or more vectors for deforming the shape model.

6. The method of claim 5, further comprising:

associating statistical data of said cancer probability map with the shape model.

7. The method of claim 6, wherein the statistical data is gathered from histological data.

8. The method of claim 1, further comprising:

transferring prostate zone information to the ultrasound image.

9. The method of claim 8, wherein transferring further comprises:

transferring statistical data associated with one or more potentially cancerous regions for at least one prostate zone.

10. The method of claim 9, further comprising:

performing a biopsy at a location within the at least one prostate zone based on the statistical data for the zone.

11. The method of claim 1, further comprising:

obtaining patient specific information; and based on the patient specific information selecting a demographically corresponding shape model for application to the ultrasound image.

12. The method of claim 1, wherein said at least one biomarker comprises a centroid of said at least one region.

13. The method of claim 1, wherein said establishing occurs before said fitting.

14. The method of claim 1, wherein said establishing occurs as part of or after said fitting.

* * * * *